United States Patent [19]
Malen et al.

[11] Patent Number: 5,229,399
[45] Date of Patent: Jul. 20, 1993

[54] AMINOMETHYLPIPERIDINE COMPOUNDS

[75] Inventors: Charles Malen, Fresnes; Guillaume de Nanteuil, Suresnes; Francis Colpaert, Vesinet, all of France

[73] Assignee: Adir et Compagnie, Courbevoie, France

[21] Appl. No.: 964,423

[22] Filed: Oct. 21, 1992

Related U.S. Application Data

[62] Division of Ser. No. 661,494, Feb. 26, 1991, Pat. No. 5,192,775.

[30] Foreign Application Priority Data

Feb. 27, 1990 [FR] France .................. 90 02394

[51] Int. Cl.⁵ .................. C07D 417/04; A61K 31/445
[52] U.S. Cl. ..................... 514/321; 546/198
[58] Field of Search .................. 546/198; 514/321

[56] References Cited

U.S. PATENT DOCUMENTS 4,291,042  9/1981  Ward .................. 546/198
5,147,881  9/1992  Howard .................. 546/198

FOREIGN PATENT DOCUMENTS 2621588  4/1989  France .................. 546/198

*Primary Examiner*—C. Warren Ivy
*Assistant Examiner*—Celia Chang
*Attorney, Agent, or Firm*—Gordon W. Hueschen

[57] ABSTRACT

The invention relates to compounds of general formula (I).

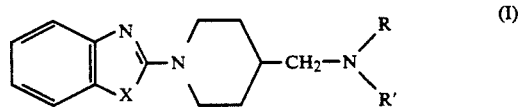

in which
- X represents an atom of sulfur or oxygen, or a substituted or unsubstituted amino group;
- R represents a hydrogen atom or any one of groups A, B, C, D, E, F or G;
- R' represents a hydrogen atom, an alkyl group or any one of groups A, B, C, D, E or F, with R'=H when R=G; or R and R' form, with the nitrogen atom to which they are attached, an optionally substituted piperazine ring.

Medicaments.

6 Claims, No Drawings

AMINOMETHYLPIPERIDINE COMPOUNDS

This application is a division of our prior-filed copending U.S. application Ser. No. 07/661,494, filed Feb. 26, 1991, now U.S. Pat. No. 5,192,775 issued Mar. 9, 1993.

The subject of the present invention is new pounds of aminomethylpiperidine.

Numerous compounds of piperidine have been described in the literature. These include the compounds mentioned in Patent FR 2,618,435 which present antihistamine properties or again in Patent FR 2,587,029 which are useful in the treatment of allergies The compounds of the present invention differ from those described in the prior art since the invention relates to compounds of 4-(aminomethyl)piperidine substituted at position 1 by a heterocyclic group.

As well as being new, they possess very valuable pharmacological properties.

They act both on the central nervous system and on the peripheral nervous system by means of the 5-HT$_{1A}$ receptors for which they have a very great affinity. This property makes them useful in the treatment of depression, anxiety, stress, schizophrenia, pain, cardio-vascular disorders, and hypertension. They can equally be used to modify eating and sexual behavior.

More specifically, the present invention relates to compounds of formula (I):

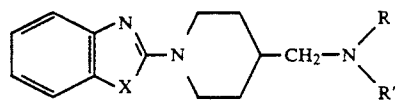

(I)

in which:
- X represents a sulfur atom, an oxygen atom, or an amino group optionally substituted by a linear or branched lower alkyl group,
- R represents a hydrogen atom or any one of the following groups:

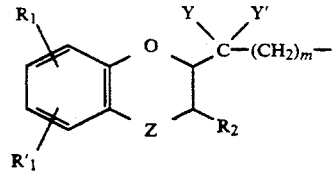

A in which:
- Z represents an oxygen atom or a CH$_2$ group,
- Y represents a hydrogen atom,
- Y' represents a hydrogen atom,
- or, Y and Y' form together an oxygen atom,
- R$_1$ represents a hydrogen atom, a halogen, a linear or branched lower alkyl group, or a linear or branched lower alkoxy group,
- R'$_1$ represents a hydrogen atom, a halogen, or a linear or branched lower alkoxy group,
- R$_2$ represents a hydrogen atom or a linear or branched lower alkyl group, and
- m is equal to 0 or 1,

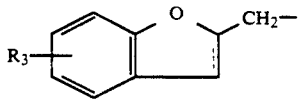

B in which R$_3$ represents a hydrogen atom, a linear or branched lower alkyl group, or a halogen,

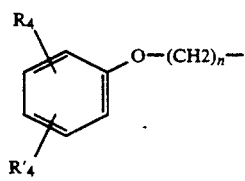

C in which:
- R$_4$ and R'$_4$, the same or different, represent a hydrogen atom, a halogen, or a linear or branched lower alkoxy group, or form together, when they are situated on two adjacent carbons, an ethylenedioxy group,
- n is equal to 2 or 3,

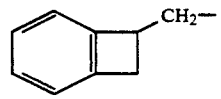

D

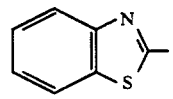

E

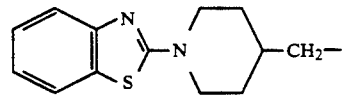

F

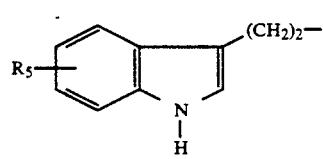

G in which:
- R$_5$ represents a hydrogen atom or a linear or branched alkoxy group (C$_1$-C$_6$), and
- R' represents a hydrogen atom, a linear or branched lower alkyl group or any one of groups A, B, C, D, E or F, with the qualification that R, represents a hydrogen atom when R represents the group G, or
- R and R' form, with the nitrogen atom to which they are attached, a piperazine ring unsubstituted or substituted on the free nitrogen of the piperazine by a phenyl group (unsubstituted or substituted by one or more halogen atoms or alkyl (C$_1$-C$_6$) or alkoxy (C$_1$-C$_6$) groups);

the term lower indicates that the groups thus qualified have 1 to 6 carbon atoms, and the dotted line in group B indicates the presence of a single or double bond, their enantiomers, diastereoisomers and epimers as well as their addition salts with a pharmaceutically acceptable acid.

Among pharmaceutically acceptable acids can be mentioned, without implied limitation, hydrochloric, sulfuric, tartaric, maleic, fumaric, oxalic, methanesulfonic and camphoric acids, etc.

The invention also extends to the process for preparing the compounds of formula (I), comprising the reaction of a compound of formula (II):

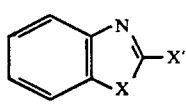
(II)

in which:

X has the same meaning as in formula (I) and X' is a halogen atom, 1/either with:

4-aminomethylpiperidine of formula (III):

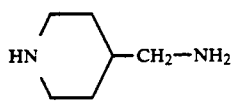
(III)

to lead to a compound of formula (I/a), a particular case of compounds of formula (I):

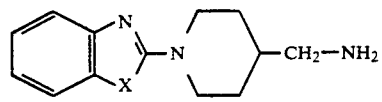
(I/a)

in which X has the same meaning as in formula (I), which is condensed on a compound of formula (IV):

 (IV)

in which $R_1$ represents any one of groups A, B, C, D, E or F, and

L is a labile group such as toluenesulfonate, methanesulfonate or a halogen atom, the isomers of which have been optionally prepared by a conventional preparation technique, to lead to a compound of formula (I/b), a particular case of compounds of formula (I)

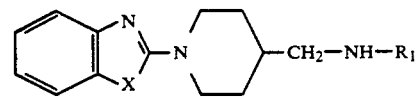
(I/b)

in which X and $R_1$ have the same meaning as above, the isomers of which are optionally separated by a conventional separation technique, which is submitted, if desired, either to the action of a compound of formula (V):

 (V)

in which L has the same meaning as above, and R'' is any one of groups A, B, C, D, E or F, to lead to a compound of formula (I/c), a particular case of compounds of formula (I)

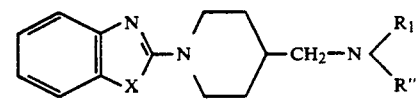
(I/c)

in which X, $R_1$ and R'' have the same meaning as above, the isomers of which are optionally separated by a conventional separation technique, or to the action of an aldehyde of formula (VI)

$$R'''—CHO \qquad (VI)$$

in which R''' is a linear or branched lower alkyl group, in the presence of a reducing agent such as sodium borohydride, sodium cyanoborohydride, hydrogen Raney nickel or formic acid, to lead to a compound of formula (I/d)

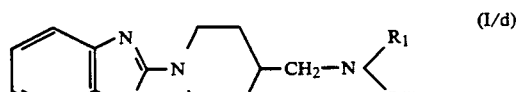
(I/d)

in which X, $R_1$ and R''' have the same meaning as above, the isomers of which are optionally separated by a conventional separation technique, 2/or with:

4-hydroxymethylpiperidine of formula (VII):

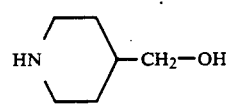
(VII)

to lead to a compound of formula (VIII):

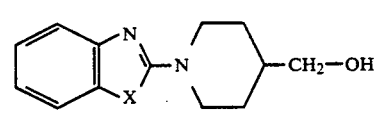
(VIII)

in which X has the same meaning as above, the isomers of which are optionally separated by a conventional separation technique, which is submitted to the action of tosyl chloride (Cl-Tos), to lead to a compound of formula (IX):

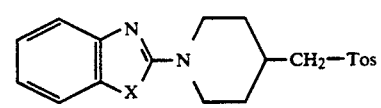
(IX)

in which X has the same meaning as above, which is reacted:

either with a compound of formula (X):

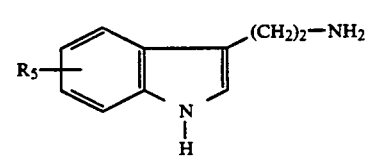
(X)

in which R: has the same meaning as in formula (I), to lead to a compound of formula (I/e), a particular case of compounds of formula (I):

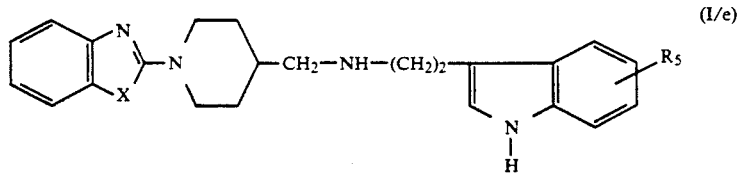

in which X and $R_5$ have the same meaning as above, the isomers of which are optionally separated by a conventional separation technique, or with a piperazine of formula (XI):

in which Ra represents a hydrogen atom or a phenyl group, unsubstituted or substituted by one or more halogen atoms, or alkyl ($C_1$-$C_6$) or alkoxy ($C_1$-$C_6$) groups, to lead to a compound of formula (I/f), a particular case of compounds of formula (I):

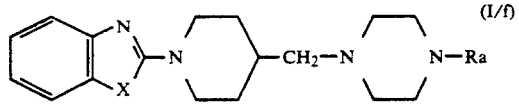

in X and Ra have the same meaning as above, the isomers of which are optionally separated by a conventional separation technique, the compounds (I/a), (I/b), (I/c), (I/d), (I/e) and (I/f) are purified by a conventional purification technique and are converted if desired into their addition salts with a pharmaceutically acceptable acid.

The compounds of formula (I) possess valuable pharmacological properties.

Binding tests showed that the compounds of the invention behaved as very powerful ligands for 5-HT$_{1A}$ receptors, with an agonist or antagonist action on the central nervous system.

The compounds of the invention, therefore, find an application in the treatment of stress (Neuropharmac., 1989, 25, (5) 471–476), anxiety, depression, schizophrenia and pain (Pharmacology and Toxicology, 1989, 64, 3–5), (Drugs of the Future, 1988, 13 (5) 429–437), (J. Neural. Transm. 1988, 74, 195-198).

Compounds which act on the 5-HT$_{1A}$ receptors can also modify eating and sexual behavior (J. Receptor Research, 1988 8, 59–81).

The subject of the present invention is also pharmaceutical compositions containing as active principle at least one compound of general formula (I) or one of their addition salts with a pharmaceutically acceptable acid, alone or in combination with one or more inert non-toxic excipients or vehicles.

Among the pharmaceutical compositions according to the invention can particularly be mentioned those which are suitable for oral, parenteral, or nasal administration, tablets or pills, sublingual tablets, capsules, suppositories, creams, dermal gels, etc.

The effective dosage varies according to the age and the weight of the patient, the nature and severity of the affection as well as the route of administration. This can be oral, nasal, rectal, or parenteral. In general the unit dosage ranges between 0.5 and 500 mg for one treatment in 1 to 3 doses in 24 hours.

The following examples illustrate the invention but do not limit it in any way.

EXAMPLE 1

1-(BENZOTHIAZOL-2-YL)-4-AMINOMETHYL-PIPERIDINE HYDROCHLORIDE 85 g of 4-aminomethylpiperidine are placed, at room temperature, in 750 ml of anhydrous toluene in the presence of 103 g of potassium carbonate and of 125 g of 2-chlorobenzothiazole. This mixture is subjected to reflux for 8 hours, then filtered and the solution evaporated under vacuum.

The residue is taken up in ethanol and after an addition of excess hydrochloric ether, the precipitate formed is spun down and washed with ether. The expected product is obtained after recrystallization from ethanol.

Melting point: 155°–160° C.

|  | Elemental microanalysis: | | | | |
|---|---|---|---|---|---|
|  | C% | H% | N% | S% | Cl% |
| Calculated: | 48.75 | 5.98 | 13.12 | 10.01 | 22.14 |
| Found: | 48.85 | 5.73 | 13.10 | 10.24 | 22.48 |

EXAMPLE 2

1-(BENZOXAZOL-2-YL)-4-AMINOMETHYL-PIPERIDINE 45 g of 4-aminomethylpiperidine are placed, at room temperature, in 500 ml of anhydrous toluene in the presence of 55 g of potassium carbonate. 50 g of 2-chlorobenzoxazole are then added at 5° C.

The mixture is heated for 2 hours at 80° C. then filtered, and the solution evaporated under vacuum.

The residue is taken up in 100 ml of ethanol, and after an addition of excess hydrochloric ether, the precipitate formed is spun down then washed with ether. This precipitate is taken up in a liter of 1 N caustic soda. The expected product is then extracted with dichloromethane. After drying, the organic phase is filtered and evaporated. The oil thus obtained is purified by chromatography on silica gel (eluting solvent: dichloromethane/methanol/ammonia: 9/1/0.1).

Melting point: 64°–66° C.

|  | Elemental microanalysis: | | |
|---|---|---|---|
|  | C% | H% | N% |
| Calculated: | 67.51 | 7.41 | 18.17 |
| Found: | 67.43 | 7.53 | 17.76 |

EXAMPLE 3

1-(BENZIMIDAZOL-2-YL)-4-AMINOMETHYL-PIPERIDINE.

45 g of 4-aminomethylpiperidine are placed in 500 ml of anhydrous toluene in the presence of 55 g of potassium carbonate and of 50 g of 2-chlorobenzimidazole. The mixture is subjected to reflux overnight. Aver evaporation and crystallization of the oily residue, the expected product is obtained after washing with dichloromethane.

Melting point: 136°–138° C.

| | Elemental microanalysis: | | |
|---|---|---|---|
| | C% | H% | N% |
| Calculated: | 67.80 | 7.88 | 24.33 |
| Found: | 67.32 | 7.90 | 24.28 |

EXAMPLE 4

1-(1-METHYLBENZIMIDAZOL-2-YL)-4-AMINOMETHYLPIPERIDINE 27 g of 4-aminomethylpiperidine are placed in 300 ml of anhydrous toluene in the presence of 33 g of potassium carbonate and of 33 g of 1-methyl-2-chlorobenzimidazole. The mixture is subjected to reflux for 48 hours. After evaporation, the residue is taken up in ether and an excess of hydrochloric ether. The precipitate formed is spun down, washed with ether, and then taken up in 750 ml of water and 30% caustic soda is added to give a basic pH.

The expected product is then extracted with dichloromethane. After drying, the organic phase is filtered and evaporated. The oil thus obtained is purified by chromatography on silica gel (eluting solvent: dichloromethane/methane/ammonia: 9/1/0.1).

Melting point: 106° C.

| | Elemental microanalysis: | | |
|---|---|---|---|
| | C% | H% | N% |
| Calculated: | 67.21 | 8.68 | 22.35 |
| Found: | 67.51 | 8.02 | 24.12 |

EXAMPLE 5

1-(BENZOTHIAZOL-2-YL)-4-[(1,4-BENZODIOXAN-2-YL)METHYLAMINOMETHYL]PIPERIDINE DIHYDROCHLORIDE

STAGE A:
1-(BENZOTHIAZOL-2-YL)-4-AMINOMETHYL-PIPERIDINE.

The compound of Example 1 is taken up in 1 N caustic soda. The expected product is then obtained after extraction with dichloromethane. After drying, the organic phase is filtered and evaporated. The oil thus obtained is taken up in boiling hexane. After cooling, the product crystallizes.

Melting point: 65°–70° C.

| | Elemental microanalysis: | | | |
|---|---|---|---|---|
| | C% | H% | N% | S% |
| Calculated: | 63.12 | 6.93 | 16.99 | 12.96 |
| Found: | 63.69 | 6.19 | 17.08 | 13.01 |

STAGE B
1-(BENZOTHIAZOL-2-YL)-4-[(1,4-BENZODIOXAN-2-YL)METHYLAMINOMETHYL]PIPERIDINE DIHYDROCHLORIDE 9 g of the compound prepared in stage A and 9 g of 2-mesyloxymethyl-1,4-benzodioxane are placed in 100 ml of anhydrous acetonitrile in the presence of 10 g of potassium carbonate. The mixture is subjected to reflux overnight, then filtered, and the solution evaporated under vacuum. The residue is taken up in 100 ml of 2 N hydrochloric acid and the solution washed several times with ether. The aqueous phase is then made alkaline with caustic soda and extracted with ethyl acetate. After drying the organic phase, filtering, and evaporating, the oil thus obtained is purified by chromatography on silica gel (eluting solvent: ether/methanol: 95/5). The expected product is obtained after addition of hydrochloric ether and precipitation and recrystallization from ethanol.

Melting point: 263° C.

| | Elemental microanalysis: | | | | |
|---|---|---|---|---|---|
| | C% | H% | N% | S% | Cl% |
| Calculated: | 56.41 | 5.81 | 8.97 | 6.84 | 15.14 |
| Found: | 56.01 | 5.78 | 8.98 | 6.92 | 15.04 |

EXAMPLE 6

1-(BENZOTHIAZOL-2-YL)-4-[(BENZOCYCLOBUTAN-1-YL)METHYLAMINOMETHYL]PIPERIDINE DIHYDROCHLORIDE

The expected product is obtained by proceeding as in Example 5 but replacing the 2-mesyloxymethyl-1,4-benzodioxane at stage B by 1-(mesyloxymethyl)benzocyclobutane (described in Tetrahedron, 1974, 1053).

Melting point: 235° C.

| | Elemental microanalysis: | | | | |
|---|---|---|---|---|---|
| | C% | H% | N% | S% | Cl% |
| Calculated: | 60.54 | 6.24 | 9.63 | 7.35 | 16.25 |
| Found: | 60.56 | 6.26 | 9.78 | 7.56 | 16.28 |

EXAMPLE 7

1-(BENZOTHIAZOL-2-YL)-4-[1,4-BENZODIOXAN-2-YL) ACETAMIDOMETHYL]PIPERIDINE HYDROCHLORIDE;

At 0° C., 10 ml of oxalyl chloride are added to 2 g of benzodioxan-2-ylcarboxylic acid in solution in 50 ml of anhydrous ether. The mixture is left overnight at room temperature, and then evaporated. The residue is taken up in 10 ml of anhydrous toluene and 2.7 g of the compound prepared at stage A of Example 5 are added at 0° C. The precipitate formed is filtered then taken up in ethanol and after an addition of excess hydrochloric ether, the expected product is obtained after filtration and recrystallization from ethanol.

Melting point: 200°–202° C.

| | Elemental microanalysis: | | | | |
|---|---|---|---|---|---|
| | C% | H% | N% | S% | Cl% |
| Calculated: | 59.25 | 5.42 | 9.42 | 7.19 | 7.95 |
| Found: | 58.95 | 5.51 | 9.34 | 7.07 | 7.85 |

EXAMPLE 8

1-(BENZOTHIAZOL-2-YL)-4-[(CHROMAN-2-YL)METHYLAMINOMETHYL]PIPERIDINE DIHYDROCHLORIDE

The expected product is obtained by proceeding as in Example 5 but replacing the 2-mesyloxymethyl-1,4-benzodioxane at stage B by 2-mesyloxymethylchromane.

Melting point: 240° C.

| | Elemental microanalysis: | | | | |
|---|---|---|---|---|---|
| | C% | H% | N% | S% | Cl% |
| Calculated: | 59.22 | 6.27 | 9.01 | 6.87 | 15.20 |
| Found: | 59.13 | 6.28 | 9.02 | 7.20 | 15.16 |

EXAMPLE 9

1-(BENZOTHIAZOL-2-YL)-4-[(7-CHLORO-1,4-BENZODIOXAN-2-YL) METHYLAMINOMETHYL]PIPERIDINE DIHYDROCHLORIDE.

The expected product is obtained by proceeding as in Example 5 but replacing the 2-mesyloxymethyl-1,4-benzodioxane at stage B by 2-mesyloxymethyl-7-chloro-1,4-benzodioxane.

Melting point: 280°–282° C.

| | Elemental microanalysis: | | | | |
|---|---|---|---|---|---|
| | C% | H% | N% | S% | Cl% |
| Calculated: | 52.54 | 5.21 | 8.36 | 6.38 | 21.15 |
| Found: | 52.88 | 5.36 | 8.40 | 6.35 | 20.90 |

EXAMPLE 10

1-(BENZOTHIAZOL-2-YL)-4-[(5-METHOXY-1,4-BENZODIOXAN-2-YL) METHYLAMINOMETHYL]PIPERIDINE DIHYDROCHLORIDE

The expected product is obtained by proceeding as in Example 5 but replacing the 2-mesyloxymethyl-1,4-benzodioxane at stage B by 2-mesyloxymethyl-5-methoxy-1,4-benzodioxane (described in J. Am. Chem. Soc. 1955, 5373).

Melting point: 248°–250° C.

| | Elemental microanalysis: | | | | |
|---|---|---|---|---|---|
| | C% | H% | N% | S% | Cl% |
| Calculated: | 55.42 | 5.86 | 8.43 | 6.43 | 14.22 |
| Found: | 55.56 | 5.93 | 8.47 | 6.59 | 14.33 |

EXAMPLE 11

1-(BENZOTHIAZOL-2-YL)-4-[(3-METHYL-1,4-BENZODIOXAN-2-YL) METHYLAMINOMETHYL]PIPERIDINE DIHYDROCHLORIDE

The expected product is obtained by proceeding as in Example 5 but by replacing the 2-mesyloxymethyl-1,4-benzodioxane at stage B by 2-mesyloxymethyl-3-methyl-1,4benzodioxane.

Melting point: 220°–228° C.

| | Elemental microanalysis: | | | | |
|---|---|---|---|---|---|
| | C% | H% | N% | S% | Cl% |
| Calculated: | 57.26 | 6.06 | 8.71 | 6.65 | 14.70 |
| Found: | 57.33 | 6.26 | 8.83 | 6.75 | 14.71 |

EXAMPLE 12

1-(BENZOTHIAZOL-2-YL)-4-[N-(1,4-BENZODIOXAN-2-YL) METHYL]-N-(METHYL)AMINOMETHYL]-PIPERIDINE DIHYDROCHLORIDE

Caustic soda is added to 1 g of the product prepared in Example 5 to give the corresponding base, which is taken up in 7.5 ml of anhydrous acetonitrile. After the addition of 1 ml of a solution of 40% formaldehyde and of 250 mg of sodium cyanoborohydride, the mixture is left under stirring for 15 minutes at room temperature. 1 ml of acetic acid is then added and the mixture is again stirred for 15 minutes at room temperature. After evaporating the solvent, adding 10 ml of 2 N caustic soda and extraction with ether, the organic phase is extracted with 3 N hydrochloric acid. The aqueous phase thus obtained is made alkaline with caustic soda and again extracted with ether. After drying and filtration, the solvent is evaporated. The expected product is obtained by precipitating the dihydrochloride in hydrochloric ether.

Melting point: 165° C.

| | Elemental microanalysis: | | | | |
|---|---|---|---|---|---|
| | C% | H% | N% | S% | Cl% |
| Calculated: | 57.26 | 6.06 | 8.71 | 6.65 | 14.70 |
| Found: | 57.21 | 6.12 | 8.46 | 6.61 | 14.39 |

EXAMPLES 13 AND 14

EXAMPLE 13

1-(BENZOTHIAZOL-2-YL)-4-[BENZOFURAN-2-YL) METHYLAMINOMETHYL]PIPERIDINE DIHYDROCHLORIDE.

The expected product is obtained by proceeding as in Example 5 but replacing the 2-mesyloxymethyl-1,4-benzodioxane at stage B by 2-chloromethylbenzofuran, and purification of the oil by chromatography on silica gel (eluting solvent: ether).

Melting point: 241°–242° C.

| | Elemental microanalysis: | | | | |
|---|---|---|---|---|---|
| | C% | H% | N% | S% | Cl% |
| Calculated: | 58.66 | 5.59 | 9.33 | 7.12 | 15.74 |

|  | Elemental microanalysis: | | | | |
| --- | --- | --- | --- | --- | --- |
|  | C% | H% | N% | S% | Cl% |
| Found: | 58.52 | 5.67 | 9.41 | 7.08 | 15.69 |

EXAMPLE 14

1-(BENZOTHIAZOL-2-YL)-4-[DI[(BENZOFURAN-2-YL)METHYL]AMINOMETHYL]PIPERIDINE DIHYDROCHLORIDE

Caustic soda is added to 1 g of the product prepared in Example 13 to give the corresponding base which is taken up in anhydrous acetonitrile. By proceeding as in stage B of Example 5 but replacing 2-mesyloxymethyl-1,4-benzodioxane by 2-chloromethylbenzofuran, the expected product is obtained.

Melting point: 183°–185° C.

|  | Elemental microanalysis: | | | | |
| --- | --- | --- | --- | --- | --- |
|  | C% | H% | N% | S% | Cl% |
| Calculated: | 64.13 | 5.38 | 7.24 | 5.52 | 12.21 |
| Found: | 64.03 | 5.48 | 7.15 | 5.52 | 12.26 |

EXAMPLE 15

1-(BENZOTHIAZOL-2-YL)-4-[[2-(2-METHOXYPHENOXY)ETHYL]AMINOMETHYL]PIPERIDINE DIHYDROCHLORIDE

The expected product is obtained by proceeding <as in Example 5 but replacing the 2-mesyloxymethyl-1,4-benzodioxane at stage B by 1-tosyloxy-2-(2-methoxyphenoxy)ethane.

Melting point: 220° C.

|  | Elemental microanalysis: | | | | |
| --- | --- | --- | --- | --- | --- |
|  | C% | H% | N% | S% | Cl% |
| Calculated: | 56.17 | 6.21 | 8.93 | 6.82 | 15.07 |
| Found: | 56.42 | 6.23 | 9.05 | 6.95 | 15.33 |

EXAMPLE 16

1-(BENZOTHIAZOL-2-YL)-4-[(8-METHOXY-1,4-BENZODIOXAN-2-YL)-METHYLAMINOMETHYL]PIPERIDINE DIHYDROCHLORIDE

The expected product is obtained by proceeding as in Example 5 but replacing the 2-mesyloxymethyl-1,4-benzodioxane at stage B by 2-tosyloxymethyl-8-methoxy-1,4-benzodioxane (described in Patent EP 210,581).

Melting point: 265°–268° C.

|  | Elemental microanalysis: | | | | |
| --- | --- | --- | --- | --- | --- |
|  | C% | H% | N% | S% | Cl% |
| Calculated: | 55.42 | 5.86 | 8.43 | 6.43 | 14.22 |
| Found: | 55.54 | 6.06 | 8.85 | 6.57 | 14.26 |

EXAMPLE 17

1-(BENXOTHIAZOL-2-yl)-4-[(6-CHLORO-1,4-BENZODIOXAN-2-YL)METHYLAMINOMETHYL]PIPERIDINE DIHYDROCHLORIDE

The expected product is obtained by proceeding as in Example 5 but replacing the 2-mesyloxymethyl-1,4-benzodioxane at stage B by 2-tosyloxymethyl-6-chloro-1,4-benzodioxane (described in Patent BE 843,995).

Melting point: 260°–264° C.

|  | Elemental microanalysis: | | | | |
| --- | --- | --- | --- | --- | --- |
|  | C% | H% | N% | S% | Cl% |
| Calculated: | 52.54 | 5.21 | 8.36 | 6.38 | 21.25 |
| Found: | 52.37 | 5.14 | 8.40 | 6.55 | 21.24 |

EXAMPLE 18

1-(BENZOTHIAZOL-2-YL)-4-[(7-METHYL-2,3-DIHYDROBENZOFURAN-2-YL)METHYLAMINOMETHYL]PIPERIDINE DIHYDROCHLORIDE

The expected product is obtained by proceeding as in Example 5 but replacing the 2-mesyloxymethyl-1,4-benzodioxane at stage B by 2-tosyloxymethyl-7-methyl-2,3dihydrobenzofuran.

Melting point: 222°–224° C.

|  | Elemental microanalysis: | | | | |
| --- | --- | --- | --- | --- | --- |
|  | C% | H% | N% | S% | Cl% |
| Calculated: | 59.22 | 6.27 | 9.01 | 6.87 | 15.20 |
| Found: | 59.09 | 6.22 | 9.05 | 6.93 | 15.25 |

EXAMPLE 19

1-(BENZOTHIAZOL-2-YL)-4-(7-CHLORO-2,3-DIHYDROBENZOFURAN-2-YL)METHYLAMINOMETHYL]PIPERIDINE DIHYDROCHLORIDE

The expected product is obtained by proceeding as in Example 5 but replacing the 2-mesyloxymethyl-1,4-benzodioxane at stage B by 2-tosyloxymethyl-7-chloro-2,3-dihydrobenzofuran.

Melting point: 212°–214° C.

|  | Elemental microanalysis | | | | |
| --- | --- | --- | --- | --- | --- |
|  | C % | H % | N % | S % | Cl % |
| Calculated: | 54.27 | 5.38 | 8.63 | 6.59 | 21.84 |
| Found: | 53.97 | 5.45 | 8.76 | 6.66 | 21.98 |

EXAMPLE 20

1-(BENZOTHIAZOL-2-YL)-4-[(7-FLUORO-2,3-DIHYDROBENZOFURAN-2-YL)METHYLAMINOMETHYL]PIPERIDINE DIHYDROCHLORIDE

The expected product is obtained by proceeding as in Example 5 but replacing the 2-mesyloxymethyl-1,4-benzodioxane at stage B by 2-tosyloxymethyl-7-fluoro-2,3-dihydrobenzofuran.

Melting point: 205°–208° C.

| Elemental microanalysis | | | | | |
|---|---|---|---|---|---|
| | C % | H % | N % | S % | Cl % |
| Calculated: | 56.17 | 5.57 | 8.93 | 6.82 | 15.07 |
| Found: | 55.95 | 5.59 | 9.15 | 6.78 | 15.31 |

EXAMPLE 21

1-(BENZOTHIAZOL-2-YL)-4-[(7-ISOPROPYL-2,3-DIHYDROBENZOFURAN-2-YL) METHYLAMINOMETHYL]PIPERIDINE DIHYDROCHLORIDE.

The expected product is obtained by proceeding as in Example 5 but replacing the 2-mesyloxymethyl-1,4-benzodioxane at stage B by 2-tosyloxymethyl-7-isopropyl-2,3-dihydrobenzofuran.

Melting point: 218°–220° C.

| Elemental microanalysis | | | | | |
|---|---|---|---|---|---|
| | C % | H % | N % | S % | Cl % |
| Calculated: | 60.72 | 6.74 | 8.50 | 6.48 | 14.34 |
| Found: | 60.56 | 6.49 | 8.62 | 6.50 | 14.39 |

EXAMPLE 22

1-(BENZOTHIAZOL-2-YL)-4-[(5-FLUORO-2,3-DIHYDROBENZOFURAN-2-YL) METHYLAMINOMETHYL]PIPERIDINE DIHYDROCHLORIDE.

The expected product is obtained by proceeding as in Example 5 but replacing the 2-mesyloxymethyl-1,4-benzodioxane at stage B by 2-tosyloxymethyl-5-fluoro-2,3-dihydrobenzofuran.

Melting point: 223°–228° C.

| Elemental microanalysis | | | | | |
|---|---|---|---|---|---|
| | C % | H % | N % | S % | Cl % |
| Calculated: | 56.17 | 5.57 | 8.93 | 6.82 | 15.07 |
| Found: | 56.16 | 5.57 | 8.91 | 6.83 | 15.02 |

EXAMPLE 23

1-(BENZOTHIAZOL-2-YL)-4-[(2,3-DIHYDROBENZOFURAN-2-YL) METHYLAMINOMETHYL]PIPERIDINE DIHYDROCHLORIDE.

The expected product is obtained by proceeding as in Example 5 but replacing the 2-mesyloxymethyl-1,4-benzodioxane at stage B by 2-tosyloxymeth-Yl-2,3-dihydrobenzofuran.

Melting point: 230°–235° C.

| Elemental microanalysis | | | | | |
|---|---|---|---|---|---|
| | C % | H % | N % | S % | Cl % |
| Calculated: | 58.40 | 6.02 | 9.29 | 7.09 | 15.67 |
| Found: | 58.46 | 5.78 | 9.18 | 7.21 | 15.72 |

EXAMPLE 24

1-(BENZOTHIAZOL-2-YL)-4-[(7-METHOXY-1,4-BENZODIOXAN-2-YL) METHYLAMINOMETHYL]PIPERIDINE DIHYDROCHLORIDE.

The expected product is obtained by proceeding as in Example 5 but replacing the 2-mesyloxymethyl-1,4-benzodioxane at stage B by 2-tosyloxymeth-Yl-7-methoxy-1,4-benzodioxane (described in J. Med. Chem., 1965, 8, 446).

Melting point: 267°–270° C.

| Elemental microanalysis | | | | | |
|---|---|---|---|---|---|
| | C % | H % | N % | S % | Cl % |
| Calculated: | 55.42 | 5.86 | 8.43 | 6.43 | 14.22 |
| Found: | 55.11 | 5.87 | 8.63 | 6.72 | 14.17 |

EXAMPLE 25

1-(BENZOTHIAZOL-2-YL)-4-[(6-METHOXY-1,4-BENZODIOXAN-2-YL) METHYLAMINOMETHYL]PIPERIDINE DIHYDROCHLORIDE.

The expected product is obtained by proceeding as in Example 5 but replacing the 2-mesyloxymethyl-1,4-benzodioxane at stage B by 2-tosyloxymethyl-6-methoxy-1,4-benzodioxane (described in J. Med. Chem., 1965, 8, 446).

Melting point: 235°–240° C.

| Elemental microanalysis | | | | | |
|---|---|---|---|---|---|
| | C % | H % | N % | S % | Cl % |
| Calculated: | 55.42 | 5.86 | 8.43 | 6.43 | 14.22 |
| Found: | 55.25 | 5.67 | 7.89 | 6.51 | 14.12 |

EXAMPLE 26

1-(BENZOTHIAZOL-2-YL)-4-[(BENZOTHIAZOL-2-YL) AMINOMETHYL]PIPERIDINE DIHYDROCHLORIDE

The expected product is obtained by proceeding as in Example 1 but placing 1 unit of 4-aminomethylpiperidine in anhydrous toluene for every two units of 2-chlorobenzothiazole at room temperature.

Melting point: 190°–195° C.

| Elemental microanalysis | | | | | |
|---|---|---|---|---|---|
| | C % | H % | N % | S % | Cl % |
| Calculated: | 52.98 | 4.89 | 12.36 | 14.14 | 15.64 |
| Found: | 53.04 | 4.85 | 12.48 | 14.20 | 15.76 |

EXAMPLE 27

1-(BENZOTHIAZOL-2-YL)-4-[(3-PHENOXY-PROPYL)-AMINOMETHYL]PIPERIDINE DIHYDROCHLORIDE

The expected product is obtained by proceeding as in Example 5 but replacing the 2-mesyloxymethyl-1,4-benzodioxane at stage B by (1-bromo-3-phenoxy)propane.

Melting point: 247°–249° C.

|  | Elemental microanalysis | | | | |
|---|---|---|---|---|---|
|  | C % | H % | N % | S % | Cl % |
| Calculated: | 58.14 | 6.43 | 9.25 | 7.06 | 15.60 |
| Found: | 58.34 | 6.38 | 9.29 | 7.16 | 15.58 |

EXAMPLE 28

1-(BENZOTHIAZOL-2-YL)-4-[(6-FLUORO-1,4-BENZODIOXAN-2-YL)METHYLAMINOMETHYL]PIPERIDINE DIHYDROCHLORIDE.

The expected product is obtained by proceeding as in Example 5 but replacing the 2-mesyloxymethyl-1,4-benzodioxane at stage B by 2-tosyloxymethyl-6-fluorobenzodioxane (described in Patent BE 843,995).

Melting point: 260°-265° C.

|  | Elemental microanalysis | | | | |
|---|---|---|---|---|---|
|  | C % | H % | N % | S % | Cl % |
| Calculated: | 54.32 | 5.39 | 8.64 | 6.59 | 11.58 |
| Found: | 54.65 | 5.40 | 8.41 | 6.56 | 14.44 |

EXAMPLE 29

1-(BENZOTHIAZOL-2-YL)-4-[[2-(2,6-DIMETHOXYPHENOXY)ETHYL]AMINOMETHYL]PIPERIDINE DIHYDROCHLORIDE

The expected product is obtained by proceeding as in Example 5 but replacing the 2-mesyloxymethyl-1,4-benzodioxane at stage B by 1-bromo-2-(2,6-dimethoxyphenoxy)ethane.

Melting point: 176°-180° C.

|  | Elemental microanalysis | | | | |
|---|---|---|---|---|---|
|  | C % | H % | N % | S % | Cl % |
| Calculated: | 55.20 | 6.24 | 8.40 | 6.41 | 14.17 |
| Found: | 54.90 | 5.77 | 8.23 | 6.65 | 14.11 |

EXAMPLE 30

1-(BENZOTHIAZOL-2-YL)-4-[[2-(4-METHOXYPHENOXY)ETHYL]AMINOMETHYL]PIPERIDINE DIHYDROCHLORIDE

The expected product is obtained by proceeding as in Example 5 but replacing the 2-mesyloxymethyl-1,4-benzodioxane at stage B by 1-bromo-2-(4-methoxyphenoxy)ethane.

Melting point: 203° C.

|  | Elemental microanalysis | | | | |
|---|---|---|---|---|---|
|  | C % | H % | N % | S % | Cl % |
| Calculated: | 56.17 | 6.21 | 8.93 | 6.82 | 15.07 |
| Found: | 56.17 | 6.21 | 8.99 | 7.03 | 14.98 |

EXAMPLE 31

1-(BENZOTHIAZOL-2-YL)-4-[[2-(3-METHOXYPHENOXY)ETHYL]AMINOMETHYL]PIPERIDINE DIHYDROCHLORIDE

The expected product is obtained by proceeding as in Example 5 but replacing the 2-mesyloxymethyl-1,4-benzodioxane at stage B by 1-bromo-2-(3-methoxyphenoxy)ethane.

Melting point: 211°-213° C.

|  | Elemental microanalysis | | | | |
|---|---|---|---|---|---|
|  | C % | H % | N % | S % | Cl % |
| Calculated: | 56.17 | 6.21 | 8.93 | 6.82 | 15.07 |
| Found: | 56.01 | 6.04 | 8.92 | 6.84 | 15.12 |

EXAMPLE 32

1-(BENZOTHIAZOL-2-YL)-4-[[(5-CHLORO-1,4-BENZODIOXAN-2-YL)METHYLAMINOMETHYL]PIPERIDINE DIHYDROCHLORIDE,.

The expected product is obtained by proceeding as in Example 5 but replacing the 2-mesyloxymethyl-1,4-benzodioxane benzodioxane (described in J. Med. Chem., 1965, 8, 446).

Melting point: 235°-238° C.

|  | Elemental microanalysis | | | | |
|---|---|---|---|---|---|
|  | C % | H % | N % | S % | Cl % |
| Calculated: | 52.54 | 5.21 | 8.36 | 6.38 | 21.15 |
| Found: | 52.77 | 5.25 | 8.32 | 6.51 | 21.14 |

EXAMPLE 33

1-(BENZOTHIAZOL-2-YL)-4-[(5,6-DICHLORO-1,4-BENZODIOXAN-2-YL)METHYLAMINOMETHYL]PIPERIDINE DIHYDROCHLORIDE.

The expected product is obtained by proceeding as in Example 5 but replacing the 2-mesyloxymethyl-1,4-benzodioxane at stage B by 2-tosyloxymethyl-5,6-dichloro-1,4-benzodioxane (described in J. Med. Chem., 1965, 8, 446).

Melting point: 269-272° C.

|  | Elemental microanalysis | | | | |
|---|---|---|---|---|---|
|  | C % | H % | N % | S % | Cl % |
| Calculated: | 49.18 | 4.69 | 7.82 | 5.97 | 26.39 |
| Found: | 48.89 | 4.81 | 7.69 | 6.00 | 26.64 |

EXAMPLE 34

1-(BENZOTHIAZOL-2-YL)-4-[[2-(BENZODIOXAN-5YLOXY)ETHYL]AMINOMETHYL]PIPERIDINE DIHYDROCHLORIDE

The expected product is obtained by proceeding as in Example 5 but replacing the 2-mesyloxymethyl-1,4-benzodioxane at stage B by 1-chloro-2-(1,4-benzodioxan-5-yloxy)ethane (described in Patent FR 1,343,644).

Melting point: 176°-178° C.

|  | Elemental microanalysis | | | | |
|---|---|---|---|---|---|
|  | C % | H % | N % | S % | Cl % |
| Calculated: | 55.42 | 5.86 | 8.43 | 6.43 | 14.22 |
| Found: | 55.22 | 6.48 | 8.20 | 6.45 | 14.23 |

EXAMPLE 35

1-(BENZOXAZOL-2-YL)-4-[(1,4-BENZODIOXAN-2YL)METHYLAMINOMETHYL]PIPERIDINE DIHYDROCHLORIDE

The expected product is obtained by proceeding as in Example 5 but replacing the 2-mesyloxymethyl-1,4-benzodioxane at stage B by 2-tosyloxymethyl--1,4-benzodioxane and the 1-(benzothiazol-2-yl)-4-aminomethylpiperidine by 1-(benzoxazol-2-yl)-4-aminomethylpiperidine prepared in Example 2.

Melting point: 260°–261° C.

| | Elemental microanalysis | | | |
|---|---|---|---|---|
| | C % | H % | N % | Cl % |
| Calculated: | 58.41 | 6.02 | 9.29 | 15.67 |
| Found: | 58.37 | 6.07 | 9.40 | 15.59 |

EXAMPLE 36

1-(BENZOTHIAZOL-2-YL)-4-[(2-PHENOXYETHYL)-AMINOMETHYL]PIPERIDINE DIHYDROCHLORIDE

The expected product is obtained by proceeding as in Example 5 but replacing the 2-mesyloxymethyl-1,4-benzodioxane at stage B by β-bromophenetol.

Melting point: 240°–242° C.

| | Elemental microanalysis | | | | |
|---|---|---|---|---|---|
| | C % | H % | N % | S % | Cl % |
| Calculated: | 57.27 | 6.18 | 9.54 | 7.28 | 16.10 |
| Found: | 57.41 | 6.08 | 9.57 | 7.39 | 16.41 |

EXAMPLE 37

1-(BENZOTHIAZOL-2-YL)-4-[[2-(2-CHLOROPHENOXY) ETHYL]AMINOMETHYL]PIPERIDINE DIHYDROCHLORIDE.

The expected product is obtained by proceeding as in Example 5 but replacing the 2-mesyloxymethyl-1,4-benzodioxane at stage B by 1-bromo-2-(2-chlorophenoxy)ethane.

Melting point: 225°–228° C.

| | Elemental microanalysis | | | | |
|---|---|---|---|---|---|
| | C % | H % | N % | S % | Cl % |
| Calculated: | 53.11 | 5.52 | 8.85 | 6.75 | 22.40 |
| Found: | 53.25 | 5.53 | 8.80 | 6.15 | 22.07 |

EXAMPLE 38

1-(BENZOTHIAZOL-2-YL)-4-[[2-(3-CHLOROPHENOXY)ETHYL]AMINOMETHYL]PIPERIDINE DIHYDROCHLORIDE

The expected product is obtained by proceeding as in Example 5 but replacing the 2-mesyloxymethyl-1,4-benzodioxane at stage B by 1-bromo-2-(3-chlorophenoxy)ethane.

Melting point: 185°–190° C.

| | Elemental microanalysis | | | | |
|---|---|---|---|---|---|
| | C % | H % | N % | S % | Cl % |
| Calculated: | 53.11 | 5.52 | 8.85 | 6.75 | 22.40 |
| Found: | 53.08 | 5.59 | 8.91 | 6.47 | 22.42 |

EXAMPLE 39

1-(BENZOTHIAZOL-2-YL)-4-[[2-(4-CHLOROAMINOMETHYL]PIPERIDINE DIHYDROCHLORIDE

The expected product is obtained by proceeding as in Example 5 but replacing the 2-mesyloxymethyl-1,4-benzodioxane at stage B by 1-bromo-2-(4-chlorophenoxy)ethane.

Melting point: 255°–260° C.

| | Elemental microanalysis | | | | |
|---|---|---|---|---|---|
| | C % | H % | N % | S % | Cl % |
| Calculated: | 53.11 | 5.52 | 8.85 | 6.75 | 22.40 |
| Found: | 53.09 | 5.42 | 8.86 | 6.72 | 22.04 |

EXAMPLE 40

1-(BENZIMIDAZOL-2-YL)-4-[(1,4-BENZODIOXAN-2YL)METHYLAMINOMETHYL]PIPERIDINE DIHYDROCHLORIDE

The expected product is obtained by proceeding as in Example 5 but replacing the 2-mesyloxymethyl-1,4-benzodioxane by 2-tosyloxymethyl-1,4-benzodioxane and the 1-(benzothiazol-2-yl)-4-aminomethylpiperidine by 1-(benzimidazol-2-yl)-4-aminomethylpiperidine prepared in Example 3.

Melting point: >260° C.

| | Elemental microanalysis | | | | |
|---|---|---|---|---|---|
| | C % | H % | N % | S % | Cl % |
| Calculated: | 58.54 | 6.25 | 12.41 | | 15.71 |
| Found: | 58.87 | 6.22 | 12.37 | | 15.79 |

EXAMPLE 41

1-(BENZOTHIAZOL-2-YL)-4-[[2-(2,6-DICHLOROPHENOXY)ETHYL]AMINOMETHYL]PIPERIDINE DIHYDROCHLORIDE

The expected product is obtained by proceeding as in Example 5 but replacing the 2-mesyloxymethyl-1,4-benzodioxane at stage B by 1-bromo-2-(2,6-dichlorophenoxy)ethane.

Melting point: 212°–216° C.

| | Elemental microanalysis | | | | |
|---|---|---|---|---|---|
| | C % | H % | N % | S % | Cl % |
| Calculated: | 49.52 | 4.95 | 8.25 | 6.30 | 27.84 |
| Found: | 49.23 | 5.05 | 8.24 | 6.63 | 27.94 |

EXAMPLE 42

1-(BENZOXAZOL-2-YL)-4-[(8-METHOXY-1,4-BENZODIOXAN-2-YL) METHYLAMINOMETHYL]PIPERIDINE DIHYDROCHLORIDE

The expected product is obtained by proceeding as in Example 35 but replacing the 2-tosyloxymethyl-1,4-benzodioxane at stage B by 2-tosyloxymethyl-8-methoxy-1,4-benzodioxane (described in Patent EP 210,581).

Melting point: 226°-228° C.

|  | Elemental microanalysis | | | | |
| --- | --- | --- | --- | --- | --- |
|  | C % | H % | N % | S % | Cl % |
| Calculated: | 57.27 | 6.06 | 8.71 | 14.70 |  |
| Found: | 56.99 | 5.98 | 8.62 | 14.81 |  |

EXAMPLE 43

1-(BENZIMIDAZOL-2-YL)-4-[(2,3-DIHYDROBENZOFURAN-2-YL) METHYLAMINOMETHYL]PIPERIDINE DIHYDROCHLORIDE

The expected product is obtained by proceeding as in Example 40 but replacing the 2-tosyloxymethyl-1,4-benzodioxane by 2-tosyloxymethyl-2,3-dihydrobenzofuran.

Melting point: 241°-245° C.

|  | Elemental microanalysis | | | |
| --- | --- | --- | --- | --- |
|  | C % | H % | N % | Cl % |
| Calculated: | 60.69 | 6.48 | 12.87 | 16.29 |
| Found: | 60.61 | 6.52 | 12.93 | 16.24 |

EXAMPLE 44

1-(BENZOXAZOL-2-YL)-4-[[2-(2-METHOXYPHENOXY) ETHYL]AMINOMETHYL]PIPERIDINE DIHYDROCHLORIDE

The expected product is obtained by proceeding as in Example 35 but replacing the 2-tosyloxymethyl-1,4-benzodioxane by 1-tosyloxy-2-(2-methoxyphenoxy)ethane.

Melting point: 200°-202° C.

|  | Elemental microanalysis | | | |
| --- | --- | --- | --- | --- |
|  | C % | H % | N % | Cl % |
| Calculated: | 58.15 | 6.43 | 9.25 | 15.60 |
| Found: | 57.97 | 6.65 | 9.10 | 15.47 |

EXAMPLE 45

1-(BENZIMIDAZOL-2-YL)-4-[[2-(2-METHOXYPHENOXY) ETHYL]AMINOMETHYL]PIPERIDINE DIHYDROCHLORIDE

The expected product is obtained by proceeding as in Example 40 but replacing the 2-tosyloxymethyl-1,4-benzodioxane by 1-tosyloxy-2-(2-methoxyphenoxy)ethane.

Melting point: 275°-280° C.

|  | Elemental microanalysis | | | |
| --- | --- | --- | --- | --- |
|  | C % | H % | N % | Cl % |
| Calculated: | 58.41 | 6.46 | 12.38 | 15.67 |
| Found: | 58.13 | 6.69 | 11.96 | 15.62 |

EXAMPLE 46

1-(BENZIMIDAZOL-2-YL)-4-[(8-METHOXY-1,4-BENZODIOXAN-2-YL) METHYLAMINOMETHYL]PIPERIDINE DIHYDROCHLORIDE

The expected product is obtained by proceeding as in Example 40 but replacing the 2-tosyloxymethyl-1,4-benzodioxane by 2-tosyloxymethyl-8-methoxy-1,4-benzodioxane (described in Patent EP 210,581).

Melting point: 315°-317° C.

|  | Elemental microanalysis | | | |
| --- | --- | --- | --- | --- |
|  | C % | H % | N % | Cl % |
| Calculated: | 57.38 | 6.28 | 11.64 | 14.73 |
| Found: | 57.34 | 6.32 | 11.51 | 14.59 |

EXAMPLE 47

1-(1-METHYLBENZIMIDAZOL-2-YL)-4-[(8-METHOXY-1,4-BENZODIOXAN-2-YL]METHYLAMINOMETHYL]PIPERIDINE DIHYDROCHLORIDE

The expected product is obtained by proceeding as in Example 5 but replacing the 2-mesyloxymethyl-1,4-benzodioxane by 2-tosyloxymethyl-8-methoxy-1,4-benzodioxane (described in Patent EP 210,581), and the 1-(benzothiazol-2-yl) -4-aminomethylpiperidine by 1-(1-methylbenzimidazol-2-yl) -4-aminomethylpiperidine obtained in Example 4.

Melting point: 265°-267° C.

|  | Elemental microanalysis | | | |
| --- | --- | --- | --- | --- |
|  | C % | H % | N % | Cl % |
| Calculated: | 58.18 | 6.51 | 11.31 | 14.31 |
| Found: | 58.28 | 6.69 | 11.15 | 14.38 |

EXAMPLE 48

1-(1-METHYLBENZIMIDAZOL-2-YL)-4-[(1,4-BENZODIOXAN-2-YL) METHYLAMINOMETHYL]PIPERIDINE DIHYDROCHLORIDE

The expected product is obtained by proceeding as in Example 47 but replacing the 2-tosyloxymethyl-8-methoxy-1,4-benzodioxane by 2-tosyloxymethyl-1,4-benzodioxane.

Melting point: 253°-255° C.

|  | Elemental microanalysis | | | |
| --- | --- | --- | --- | --- |
|  | C % | H % | N % | Cl % |
| Calculated: | 59.36 | 6.50 | 12.04 | 15.23 |
| Found: | 59.55 | 6.70 | 11.95 | 15.34 |

EXAMPLE 49

1-(BENZOTHIAZOL-2-YL)-4-[[3-(2,6-DIMETHOXYPHENOXY)PROPYL]AMINOMETHYL]PIPERIDINE DIHYDROCHLORIDE

The expected product is obtained by proceeding as in Example 5 but replacing the 2-mesyloxymethyl-1,4-benzodioxane at stage B by 1-bromo-3-(2,6-dimethoxyphenoxy)propane.

Melting point: 205°–207° C.

| | Elemental microanalysis | | | | |
|---|---|---|---|---|---|
| | C % | H % | N % | S % | Cl % |
| Calculated: | 56.03 | 6.46 | 8.17 | 6.23 | 13.78 |
| Found: | 55.71 | 6.71 | 8.06 | 6.35 | 13.90 |

EXAMPLE 50

1-(1-METHYLBENZIMIDAZOL-2-YL)-4-[[2-(2METHOXYPHENOXY)ETHYL]AMINOMETHYL]PIPERIDINE DIHYDROCHLORIDE

The expected product is obtained by proceeding as in Example 47 but replacing the 2-tosyloxymethyl-8-methoxy-1,4-benzodioxane at stage B by 1-tosyloxy-2-(2methoxyphenoxy)ethane.

Melting point: 270–274° C.

| | Elemental microanalysis | | | |
|---|---|---|---|---|
| | C % | H % | N % | Cl % |
| Calculated: | 59.10 | 6.90 | 11.99 | 15.17 |
| Found: | 59.24 | 7.01 | 12.01 | 15.10 |

EXAMPLE 51

1-(BENZOTHIAZOL-2-YL)-4-[(8-CHLORO-1,4-BENZODIOXAN-2-YL)METHYLAMINOMETHYL]PIPERIDINE DIHYDROCHLORIDE

The expected product is obtained by proceeding as in Example 5 but replacing the 2-mesyloxymethyl-1,4-benzodioxane at stage B by 2-tosyloxymethyl-8-methoxy-1,4-benzodioxane (described in J. Med. Chem. 1965, 8, 446).

Melting point: 220°–222° C.

| | Elemental microanalysis | | | | |
|---|---|---|---|---|---|
| | C % | H % | N % | S % | Cl % |
| Calculated: | 52.54 | 5.21 | 8.36 | 6.44 | 21.15 |
| Found: | 52.63 | 5.24 | 8.03 | 6.38 | 21.08 |

EXAMPLE 52

1-(BENZOTHIAZOL-2-YL)-4-[[2-(1,4-BENZODIOXAN-2-YL)ETHYL]AMINOMETHYL]PIPERIDINE DIHYDROCHLORIDE

The expected product is obtained by proceeding as in Example 5 but replacing the 2-mesyloxymethyl-1,4-benzodioxane at stage B by 2-tosyloxyethyl-1,4-benzodioxane.

Melting point: 260°–264° C.

| | Elemental microanalysis | | | | |
|---|---|---|---|---|---|
| | C % | H % | N % | S % | Cl % |
| Calculated: | 57.26 | 6.06 | 8.71 | 6.65 | 14.70 |
| Found: | 57.16 | 5.95 | 8.62 | 6.86 | 14.81 |

EXAMPLE 53

N,N-DI[[1-(BENZOTHIAZOL-2-YL)PIPERIDIN-4YL]METHYL]AMINE TRICHLOROHYDRIDE

STAGE A:
1-(BENZOTHIAZOL-2-YL)-4-HYDROXYMETHYLPIPERIDINE 30 g of 4-hydroxymethylpiperidine, 44 g of 2-chlorobenzothiazole and 72 g of potassium carbonate are reacted in 600 ml of acetonitrile under reflux overnight. After filtration and evaporation of the solvent, the residue is taken up in 200 ml of ethyl acetate and extracted with 1 N hydrochloric acid. The aqueous phase is made alkaline with caustic soda and extracted with dichloromethane. The expected product is obtained by drying and evaporation.

Melting point: 76°–80° C.

STAGE B:
1-(BENZOTHIAZOL-2-YL)-4-TOSYLOXYMETHYLPIPERIDINE

After dissolving the compound obtained at stage A in pyridine and adding an equivalent amount of tosyl chloride, the reaction mixture is stirred overnight at room temperature. The expected product is obtained after washing with diluted hydrochloric acid and with water.

Melting point: 184° C.

STAGE C:
N,N-DI[[1-BENZOTHIAZOL-2-YL)PIPERIDIN-4YL]METHYL]AMINE TRIHYDROCHLORIDE

The expected product is obtained by proceeding as in Example 5 but replacing the 2-mesyloxymethyl-1,4-benzodioxane by 1-(benzothiazol-2-yl)-4-tosyloxymethylpiperidine obtained in the preceding stage.

Melting point: 265°–270° C.

| | Elemental microanalysis | | | | |
|---|---|---|---|---|---|
| | C % | H % | N % | S % | Cl % |
| Calculated: | 53.19 | 5.84 | 11.93 | 10.92 | 18.12 |
| Found: | 53.62 | 5.96 | 11.92 | 10.90 | 17.72 |

EXAMPLE 54

1-(BENZOXAZOL-2-YL)-4-[(2,3-DIHYDROBENZOFURAN-2-YL)METHYLAMINOMETHYL]PIPERIDINE DIHYDROCHLORIDE

The expected product is obtained by proceeding as in Example 35 but replacing the 2-tosyloxymethyl-1,4-benzodioxane at stage B by 2-tosyloxynethyl-2,3-dihydrobenzofuran.

Melting point: 228°–230° C.

| | Elemental microanalysis | | | |
|---|---|---|---|---|
| | C % | H % | N % | Cl % |
| Calculated: | 60.55 | 6.24 | 9.63 | 16.25 |

| | Elemental microanalysis | | | |
|---|---|---|---|---|
| | C % | H % | N % | Cl % |
| Found: | 60.62 | 6.43 | 9.58 | 15.94 |

EXAMPLE 55

1-(BENZOTHIAZOL-2-YL)-4-[(5,8-DIMETHOXY-1,4-BENZODIOXAN-2-YL) METHYLAMINOMETHYL]PIPERIDINE DIHYDROCHLORIDE

The expected product is obtained by proceeding as in Example 5 but replacing the 2-mesyloxymethyl-1,4-benzodioxane at stage B by 2-tosyloxymeth-yl-5,8-dimethoxy-1,4-benzodioxane (described in J. Chem. Soc., Perkin Trans I, 1987, 2017–22).

Melting point: 240°–245° C.

| | Elemental microanalysis | | | | |
|---|---|---|---|---|---|
| | C % | H % | N % | S % | Cl % |
| Calculated: | 54.54 | 5.91 | 7.95 | 6.07 | 13.42 |
| Found: | 54.62 | 5.86 | 7.82 | 6.09 | 13.34 |

EXAMPLE 56

1-(2-METHOXYPHENYL)-4-[[1-(BENZOTHIAZOL-2-YL) PIPERIDIN-4-YL]METHYL]PIPERAZINE 6 g of the compound described at stage B of Example 53, 2.9 g of 1-(2-methoxyphenyl)piperazine and 4.8 g of potassium carbonate are reacted in 90 ml of acetonitrile under reflux overnight. After filtration and evaporation of the solvents, the residue is taken up in 20 ml of 2 N hydrochloric acid, and the solution is washed several times with ether. After making the aqueous phase alkaline with caustic soda it is extracted with methylene chloride. The expected product is obtained after drying and evaporating the solvent.

Melting point: 150°–152° C.

| | Elemental microanalysis | | | |
|---|---|---|---|---|
| | C % | H % | N % | S % |
| Calculated: | 68.21 | 7.16 | 13.26 | 7.59 |
| Found: | 68.15 | 7.32 | 13.33 | 7.51 |

EXAMPLE 57

1-(BENZOTHIAZOL-2-YL)-4-[2-[(INDOL-3-YL)-ETHYL]AMINOMETHYL]PIPERIDINE DIHYDROCHLORIDE

By proceeding as in Example 56 but replacing the 1-(2-methoxyphenyl)piperazine by tryptamine, the expected product is obtained in its basic form, which is converted to dihydrochloride by addition of hydrochloric ether, and crystallized in ethanol.

Melting point: 278°–282° C.

| | Elemental microanalysis | | | | |
|---|---|---|---|---|---|
| | C % | H % | N % | S % | Cl % |
| Calculated: | 59.61 | 6.09 | 12.09 | 6.92 | 15.30 |
| Found: | 59.23 | 6.13 | 11.96 | 6.91 | 15.03 |

EXAMPLE 58

1-(BENZOTHIAZOL-2-YL)-4-[[2-(5-METHOXYINDOL-3-YL) ETHYL]AMINOMETHYL]PIPERIDINE DIHYDROCHLORIDE

The expected product is obtained by proceeding as in Example 57 but replacing the tryptamine by 5-methoxytryptamine.

Melting point: 250°–254° C.

| | Elemental microanalysis | | | | |
|---|---|---|---|---|---|
| | C % | H % | N % | S % | Cl % |
| Calculated: | 58.29 | 6.32 | 11.33 | 6.48 | 14.34 |
| Found: | 58.48 | 6.36 | 11.25 | 6.53 | 14.13 |

EXAMPLE 59

(+)-1-(BENZOTHIAZOL-2-YL)-4-[(1,4-BENZODIOXAN-2-YL) METHYLAMINOMETHYL]PIPERIDINE

STAGE A:
(+)-2-HYDROXYMETHYL-1,4-BENZODIOXANE

The expected product is obtained from catechol and S-(+)-glycidyl tosylate by following the technique described by A. DELGADO et al. (Tetrahedron Letters, 1988, 3671–4).

Melting point: 70° C.

STAGE B:
(+)-2-TOSYLMETHYL-1,4-BENZODIOXANE

After dissolving the compound obtained at stage A in pyridine and adding an equivalent amount of tosyl chloride, the mixture is stirred for 48 hours at room temperature. The expected product is obtained after washing with diluted hydrochloric acid then with sodium bicarbonate and finally with water.

Melting point: 60° C.

STAGE C:
(+)-1-BENZOTHIAZOL-2-YL)-4-[(1,4-BENZODIOXAN-2-YL) METHYLAMINOMETHYL]PIPERIDINE

The expected product is obtained by proceeding as at stage B of Example 5, but replacing the 2-mesyloxymethyl-1,4-benzodioxane by the product obtained in the preceding stage.

Melting point: 132° C.

Optical rotation: $\alpha^{20°}{}_D = +89.8°$ (C=10 mg/ml/CHCl$_3$).

| | Elemental microanalysis | | | |
|---|---|---|---|---|
| | C % | H % | N % | S % |
| Calculated: | 66.81 | 6.37 | 10.62 | 8.11 |
| Found: | 66.44 | 6.49 | 10.78 | 8.25 |

EXAMPLE 60

1(-)-1-(BENZOTHIAZOL-2-YL)-4-[(1,4-BENZODIOXAN-2-YL) METHYLAMINOMETHYL]PIPERIDINE

The expected product is obtained by proceeding as in Example 59 but replacing at stage A (S)-(+)-glycidyl tosylate by (R)-(-)-glycidyl tosylate.

Melting point: 131° C.

Optical rotation: $\alpha^{20°}$ $C_{·D} = -89.9°$ (C=10 mg/ml/CHCl$_3$)

| | Elemental microanalysis | | | |
|---|---|---|---|---|
| | C % | H % | N % | S % |
| Calculated: | 66.81 | 6.37 | 10.62 | 8.11 |
| Found: | 66.57 | 6.30 | 10.70 | 8.20 |

PHARMACOLOGICAL STUDIES OF THE DERIVATIVES OF THE INVENTION

EXAMPLE 61

TEST OF AFFINITY FOR 5-HT$_{1A}$ RECEPTORS IN VITRO

The affinity of the compounds of the invention for 5-HT$_{1A}$ receptors was measured relative to that of 8-hydroxy-2-(dipropylamino)tetraline (8-OH-DPAT) which has a very great affinity for the 5-HT$_{1A}$ sites combined with a great selectivity.

The tests were carried out on tissue from the hippocampus of decapitated male Wistar rats. The rats were sacrificed 48 hours before the experiment and the isolated tissues were preserved at −86° C.

In order to prepare the membranes, the tissues were homogenized at 0° C. in 20 volumes of 50 mM Tris HCl buffer solution (pH 7.7, adjusted with 5 N HCl at 25° C.), with a Polytron homogenizer for 6 seconds. The whole was then centrifuged (35,000 g for 20 minutes at 4° C). Homogenization followed by centrifugation was repeated a second time under the same conditions. The pellet thus obtained was suspended for a final time in 20 volumes of the above buffer, incubated for 15 minutes at 37° C., then again centrifuged. The final pellet was then suspended in 100 volumes of the incubation buffer (Tris 50 mM, pargyline 10 μM, CaCl$_2$ 4 mM, ascorbic acid 0.1% (w/v), pH adjusted to 7.7 with 5 N HCl at 25° C.).

The compounds to be tested were put into solution in the incubation buffer. Test solutions were prepared by placing in 12×75 mm glass tubes, 10 μl of the solution of the compounds to be tested, 100 μl of a solution containing 0.4 mM of [$^3$H]-8-OH-DPAT (specific radioactivity 205 Ci/mmol). Non-specific binding was determined with the aid of a solution of 5-hydroxytryptamine (10 μM), and represented 5 to 10% of the final binding. The tubes were incubated for 30 minutes at 37° C. The solutions were then filtered through glass fiber filters pretreated with 0.1% of polyethyleneimine. The filters were then rinsed twice with 5 ml of the incubation buffer at 4° C., then placed in scintillation vials to which was added "Picofluor" scintillation liquid. Radioactivity was then determined with the aid of external standards.

The pKi values were determined by the CheungPrusoff equation:

$$pKi = -\log\left(\frac{IC\ 50}{1 + ([3H]\ 8\text{-OH-DPAT}/Kd)}\right)$$

The compounds of the invention had a great affinity for the 5-HT$_{1A}$ sites. The compound of Example 16 had a pKi equal to 9.3; that of Example 44 was equal to 9.0.

EXAMPLE 62

IN VIVO TEST OF "TAIL-FLICKS"

The potential of the compounds of the invention to act in vivo on the 5-HT$_{1A}$ receptors was brought out following a method perfected by Millan et al. (Neurosci. Lett., 1989, 107, 227–232). Subcutaneous injection of 8-OH-DPAT induces in the rat, under vacuum, marked spontaneous movements of the tail. This model then was used to evaluate the potential of the compounds of the invention administered by subcutaneous injection, to interact with the 5-HT$_{1A}$ receptors in the rat. The ED$_{50}$, that is the amount which reduces the action of 8-OH-DPAT by 50%, was thus determined.

This was equal for example, to 0.31 mg/kg for the compounds of Examples 16 and 44, which implies that, in this test, these compounds have antagonist properties towards the 5-HT$_{1A}$ receptors.

EXAMPLE 63

PHARMACEUTICAL COMPOSITION

Tablet: formulation for 1000 tablets giving 2 mg of active principle.

| | |
|---|---|
| 1-(Benzothiazol-2-yl)-4-[(8-methoxy-1,4-benzodioxan-2-yl)methylaminomethyl]-piperidine dihydrochloride | 2 g |
| Hydroxypropylcellulose | 2 g |
| Wheat starch | 10 g |
| Lactose | 100 g |
| Magnesium stearate | 3 g |
| Talc | 3 g |

We claim:

1. A compound selected from these of formula (I):

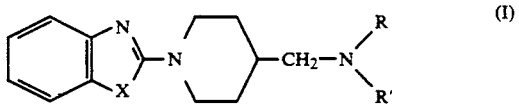

(I)

in which:

X represents sulfur,

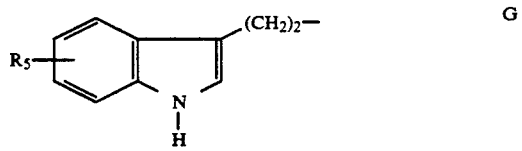

G in which:

R$_5$ represents hydrogen or linear or branched alkoxy (C$_1$–C$_6$), and

R' represents hydrogen, or linear or branched lower alkyl, wherein the term lower indicates that the groups thus qualified have 1 to 6 carbon atoms, as well as its enantiomers, diastereoisomers, and epimers and an addition salts thereof with a pharmaceutically-acceptable acid.

2. A compound as claimed in claim 1, wherein R represents an optionally substituted (indol-3-yl)ethyl group, its enantiomers, diastereoisomers and epimers as well as its addition salts with a pharmaceutically acceptable acid.

3. The compound as claimed in claim 1, which is 1-(benzothiazol-2-yl)-4-[[(2-(5-methoxyindol-3-yl)

ethyl]aminomethyl]piperidine, its enantiomers as well as its addition salts with a pharmaceutically acceptable acid.

4. The compound as claimed in claim 1, which is 1-(benzothiazol-2-yl)-4-[2[(indol-3-yl)-ethyl]aminomethylpiperidine, its enantiomers as well as its addition salts with a pharmaceutically-acceptable acid.

5. A method for treating a living animal or human, afflicted with pain, comprising the step of administering to the said living animal or human an amount of a compound of claim 1 which is effective for alleviation of said condition.

6. A pharmaceutical composition useful in the treatment of pain, containing as active principle an effective amount of a compound as claimed in claim 1, in combination with a pharmaceutically-acceptable excipient or vehicle.

* * * * *

UNITED STATES PATENT AND TRADEMARK OFFICE
CERTIFICATE OF CORRECTION

PATENT NO. : 5,229,399

DATED : Jul. 20, 1993

INVENTOR(S) : Charles Malen, Guillaume de Nanteuil, Francis Colpaert

It is certified that error appears in the above-indentified patent and that said Letters Patent is hereby corrected as shown below:

Column 1, line 9; "pounds" should read -- compounds --.
Column 4, line 56; "(X}:" should read --(X): --.
Column 4, line 66; "R:" should read -- $R_5$ --.
Column 5, line 32; "in X" should read -- in which X --.
Column 10, line 11; "1,4benzodioxane." should read
    -- 1,4-benzodioxane. --.
Column 12, line 3; "1-(BENXOTHIAZOL-" should read
    -- 1-(BENZOTHIAZOL---.
Column 12, approximately line 30; "2,3dihydrobenzofuran." should read -- 2,3-dihydrobenzofuran. --.
Column 13, line 59; "2-tosyloxymeth-Yl-" should read
    -- 2-tosyloxymethyl- --.
Column 16, approximately line 20; "zodioxane benzodioxane" should read -- zodioxane at stage B by 2-tosyloxymethyl-5-chloro-1,4-benzodioxane --.
Column 16, line 54; "AN-5YLOXY)" should read --AN-5-YLOXY)--.
Column 17, line 4; "2YL)" should read -- 2-YL) --
Column 17, lines 48, 49; move the "e" at the end of line 48 to the beginning of line 49 and insert before "thane."
Column 18, line 12; "CHLOROAMINOMETHYL]" should read
    -- CHLOROPHENOXY)ETHYL]AMINOMETHYL] --.
Column 18, line 17,18; move the "e" at the end of line 17 to the beginning of line 18 and insert before "thane."
Column 18, line 31; "2YL" should read -- 2-YL --.
Column 22, line 61; "2-tosyloxynethyl -" should read
    -- 2-tosyloxymethyl-  --.

UNITED STATES PATENT AND TRADEMARK OFFICE
CERTIFICATE OF CORRECTION

PATENT NO. : 5,229,399
DATED : Jul. 20, 1993
INVENTOR(S) : Charles Malen, Guillaume de Nanteuil, Francis Colpaert It is certified that error appears in the above-indentified patent and that said Letters Patent is hereby corrected as shown below:

Column 23, approximately line 16; "2-tosyloxymeth-yl-" should read -- 2-tosyloxymethyl- --.
Column 24, approximately line 52; " $\alpha^{20°}{}_D = +89.8°$ " should read -- $\alpha_D^{20°C} = +89.8°$ --.

Column 25, line 2; " $\alpha^{20°}{}_D = -89.9°$ " should read -- $\alpha_D^{20°C} = -89.9°$ --.

Column 26, Example 63, in the table, approximately line three; last column "piperidine dihydrochloride" should read -- piperidine dihydrochloride        2g --.
Column 26, line 36; "these" should read -- those --.

Column 26, line 44; after "sulfur," insert --R represents--.
Column 26, line 60; "and an addition" should read -- and addition --.

Signed and Sealed this

Twenty-fourth Day of May, 1994

Attest:

BRUCE LEHMAN

Attesting Officer                    Commissioner of Patents and Trademarks